(12) United States Patent
Nampalli et al.

(10) Patent No.: US 6,855,503 B2
(45) Date of Patent: Feb. 15, 2005

(54) HETEROCYCLIC FRETDYE CASSETTES FOR LABELING BIOLOGICAL MOLECULES AND THEIR USE IN DNA SEQUENCING

(75) Inventors: Satyam Nampalli, Belle Mead, NJ (US); Weihong Zhang, Highland Park, NJ (US); Sudhakar Rao, Belle Mead, NJ (US); Shiv Kumar, Belle Mead, NJ (US)

(73) Assignee: Amersham Biosciences Corp, Piscataway, NJ (US)

( * ) Notice: Subject to any disclaimer, the term of this patent is extended or adjusted under 35 U.S.C. 154(b) by 0 days.

(21) Appl. No.: 10/326,039

(22) Filed: Dec. 20, 2002

(65) Prior Publication Data

US 2004/0126763 A1 Jul. 1, 2004

(51) Int. Cl.[7] .............................. C12Q 1/68; C07D 1/02
(52) U.S. Cl. ................ 435/6; 536/23.1; 544/1
(58) Field of Search ............................ 435/6; 536/23.1; 544/1

(56) References Cited

U.S. PATENT DOCUMENTS 5,863,727 A    1/1999   Lee et al.
6,008,373 A   12/1999   Waggoner et al.
6,150,107 A   11/2000   Glazer et al.

OTHER PUBLICATIONS

Lasken et al. Proc. Natl. Acad. Sci. USA, vol. 82, pp. 1301–1305, Mar. 1985.*

* cited by examiner

*Primary Examiner*—Jezia Riley
(74) *Attorney, Agent, or Firm*—Stephen G. Ryan; Royal N. Ronning, Jr.; Yonggang Ji

(57) ABSTRACT

Exploitation of suitably functionalized heterocyclic molecules, in the design and synthesis of Fluorescence Resonance Energy Transfer (FRET) cassettes and their corresponding dideoxynucleotide terminators culminated into efficient reagents for DNA sequencing. Additionally, these FRET cassettes/terminators, of the present invention, derived from different classes of heterocyclic systems have high potential to be used for general labelling of biological molecules to generate highly sensitized signals. Their preparation, energy transfer efficiency, and use as labels, specifically, in DNA sequencing reactions is disclosed.

19 Claims, 3 Drawing Sheets

Acceptor Dye: Rhodamine 110 (R110), Rhodamine 6G (R6G), Tetramethyl Rhodamine (TAMRA), Rhodamine-X (ROX), Texas Red, Cy3, Cy3.5, Cy5, Cy5.5, Cy7 and other related dyes BASE: Cytosine, Guanine, Uracil, Thymine, Adenine, Hypoxanthine, 2-aminopurine, 2,6-diaminopurine, 7-deaza-purine, 7-Deaza-adenine, 7-Deaza-guanine, 7-deaza-hypoxanthine and other modified bases n = 0 - 3

General synthetic scheme for the synthesis of piperidine linker derived FRET cassettes and labeling dideoxynucleoside-5'-triphosphates.

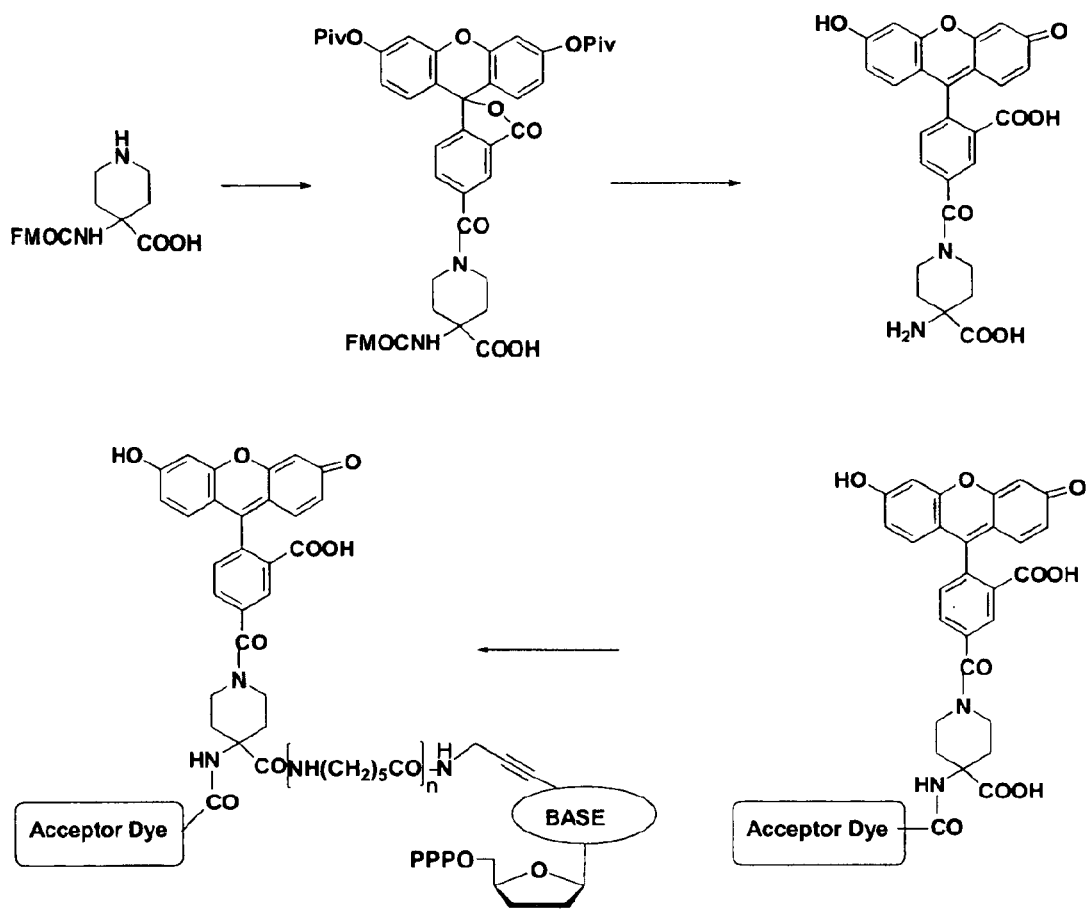

Acceptor Dye: Rhodamine 110 (R110), Rhodamine 6G (R6G), Tetramethyl Rhodamine (TAMRA), Rhodamine-X (ROX), Texas Red, Cy3, Cy3.5, Cy5, Cy5.5, Cy7 and other related dyes BASE: Cytosine, Guanine, Uracil, Thymine, Adenine, Hypoxanthine, 2-aminopurine, 2,6-diaminopurine, 7-deaza-purine, 7-Deaza-adenine, 7-Deaza-guanine, 7-deaza-hypoxanthine and other modified bases n = 0 - 3

Figure 1: General synthetic scheme for the synthesis of piperidine linker derived FRET cassettes and labeling dideoxynucleoside-5'-triphosphates.

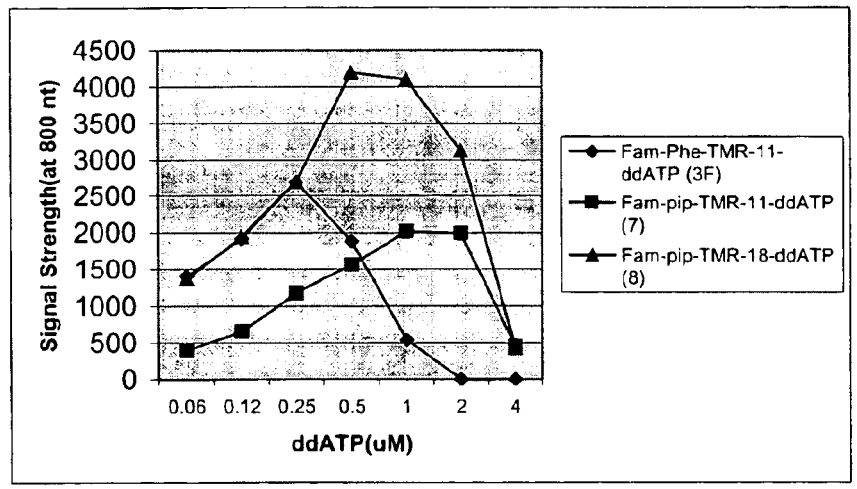
Figure 2: Signal Strength at 800 nucleotide with different concentration of TAMRA labeled ddATP of different linker structure and lengths.
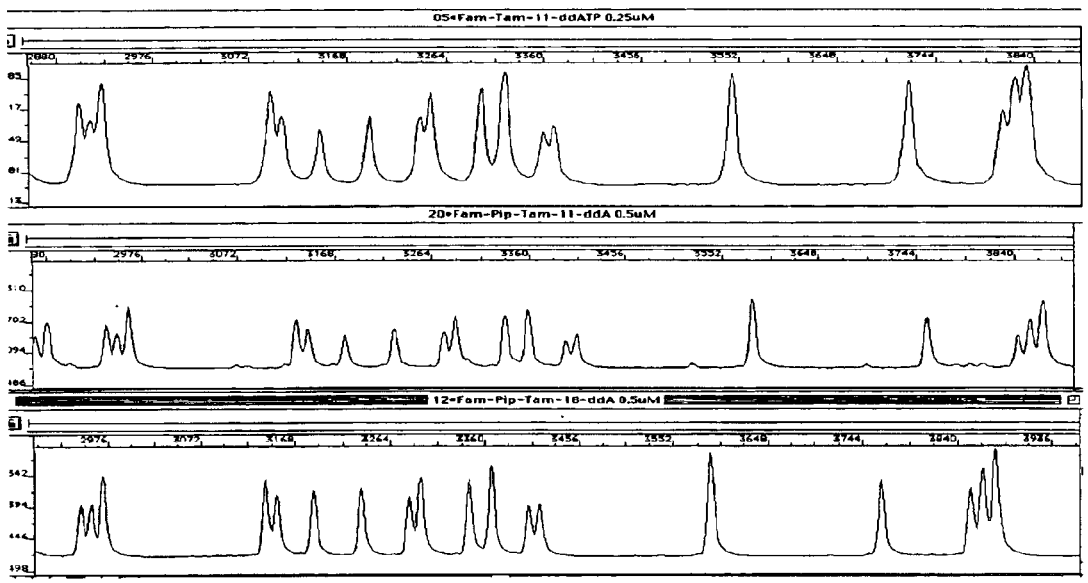
Figure 3: Single color electropherogram of FAM-Phe-TAMRA-11-ddATP (3F), FAM-Piperidine-TAMRA-11-ddATP (7), and FAM-Piperidine-TAMRA-18-ddATP (8) terminated amplicons.

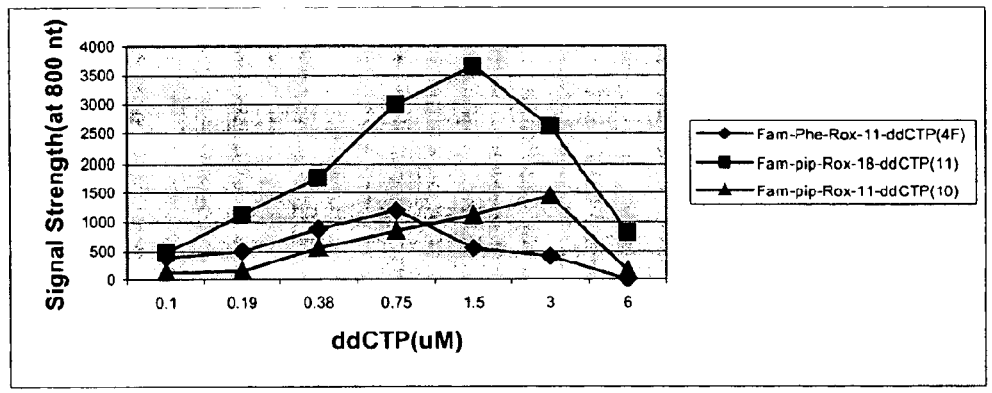
Figure 4: Signal Strength at 800 nucleotide with different concentration of ROX labeled ddCTP of different linker structure and lengths.
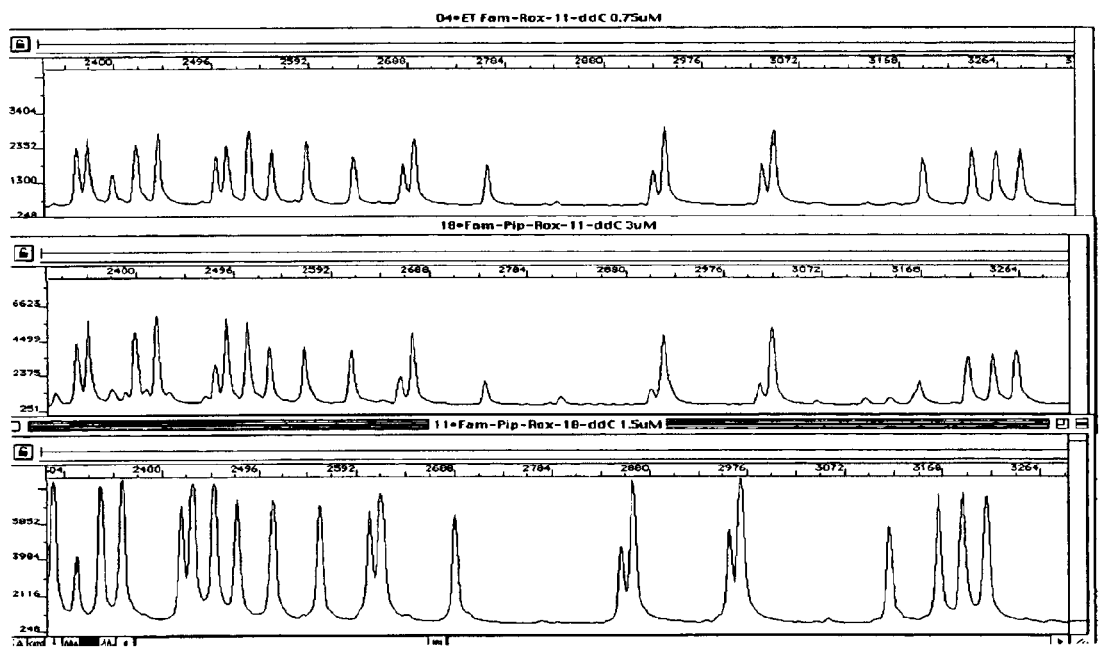
Figure 5: Single color electropherogram of FAM-Phe-ROX-11-ddCTP (4F), FAM-Piperidine-ROX-11-ddCTP (10), and FAM-Piperidine-ROX-18-ddCTP (11) terminated amplicons.

HETEROCYCLIC FRET DYE CASSETTES FOR LABELING BIOLOGICAL MOLECULES AND THEIR USE IN DNA SEQUENCING

BACKGROUND OF INVENTION

1. Field of the Invention

The present invention relates to novel heterocyclic FRET (fluorescence resonance energy transfer) cassettes, which can be used to label nucleic acids and proteins for a wide variety of molecular biology and DNA sequencing applications.

The currently accepted practice of high throughput gene sequencing employs, as a general rule, four differently labeled Energy Transfer (ET) dye terminators based on the Forster Resonance Energy Transfer (FRET) mechanism to read out the sequence by exciting at one excitation wavelength of the donor and measuring the emissions at the wavelength of the four acceptors conjugated to the four individual nucleic acid bases.

However, the currently available ET terminator sets suffer from low brightness. This low brightness is due to the inefficiencies in the transfer of energy absorbed by the donor to the acceptors and re-emitance at the emission wavelength of the acceptor. This inefficiency arises because of the structural linkages used to join the donor and the acceptors as well as the bases together to form the dye terminators are less than optimal.

The FRET efficiency mainly depends upon the relative dipole-induced-dipole orientation of the participating dyes. The functional groups' orientations with which these dyes are covalently bonded onto the core linker molecule would determine the relative dipole-dipole orientations of the dyes. Heterocyclic and alicyclic molecules with suitable functional groups for making covalent bonds with fluorescent dyes and a molecule of biological interest would serve as cassette cores by virtue of orienting the functional groups in 3D, thereby defining fixed positions for the attached groups. In order to derive highly efficient FRET dye cassettes and turn them into highly sensitive DNA sequencing terminators, heterocyclic systems with different structures and ring sizes were chosen to serve as the core cassette molecules.

In this invention, we offer a novel set of dye labeled cassettes and the corresponding terminators which is brighter than the currently available terminators. The increase in brightness for the set of dye terminators of this invention and the corresponding improvement in signal to noise allow sequencing of a broader range of DNA templates. The novel fluorophore/linker combination, in the form of piperidine or piperazine aminoacid as the core molecule, disclosed in this invention, allows the construction of brighter ET dyes. The heterocyclic FRET cassettes disclosed in this invention can be used to label nucleic acids, proteins, carbohydrates and other biological molecules of interest.

2. Description of Related Art

A large number of fluorescent dyes have been recently developed for labeling and detecting components in biological samples. Generally, these fluorescent dyes must have high extinction coefficient and quantum yield so a low detection limit can be achieved.

One class of dyes which have been developed to give large and different Stokes shifts, based on the Foster Resonance Energy Transfer (FRET) mechanism and used in the simultaneous detection of differently labeled samples in a mixture, are the ET (Energy Transfer) dyes. These ET dyes include a complex molecular structure consisting of a donor fluorophore and an acceptor fluorophore as well as a labeling function to allow their conjugation to biomolecules of interests. Upon excitation of the donor fluorophore, the energy absorbed by the donor is transferred by the Forster Resonance Energy Transfer (FRET) mechanism to the acceptor fluorophore and causes it to fluoresce. Different acceptors can be used with a single donor to form a set of ET dyes so that when the set is excited at one single donor frequency, various emissions can be observed depending on the choice of the acceptors. Upon quantification of these different emissions, the components of a mixture can readily be resolved when these dyes are conjugated to biomolecules of interest. These ET dye sets constitute the backbone of current high throughput gene sequencing methodology.

Previously, a variety of combinations of bi-fluorophore dyes have been described. U.S. Pat. No. 5,688,648, entitled "Probes Labelled with Energy Transfer Coupled Dyes" Mathies et.al., U.S. Pat. No. 5,728,528, entitled "Universal spacer/energy transfer dyes, and U.S. Pat. No. 6,150,107, entitled "Methods of sequencing and detection using energy transfer labels with cyanine dyes as donor chromophores" which are incorporated herein by reference in its entirety, including any drawings, discloses sets of fluorescent labels carrying pairs of donor and acceptor dye molecules wherein the labels can be attached to nucleic acid backbone for sequencing. The nucleic acid bases or the abasic sugar units are used as spacers to separate the donor and acceptor dyes. The optimum distance for efficient energy transfer from the donor dye to the acceptor dye was found to be ~6–10 bases. Included is a method for identifying and detecting nucleic acids in a multi-nucleic acid mixture by using different fluorescent labels, wherein the fluorescent moieties are selected from families such as cyanine dyes and xanthenes. The fluorescent labels comprise pairs of fluorophores where one fluorophore donor has emission spectra, which overlaps the fluorophore acceptor's absorption so that there is energy transfer from the excited member to the other member of the pair.

U.S. Pat. No. 6,008,373, entitled "Fluorescent labeling complexes with large stokes shift formed by coupling together cyanine and other fluorochromes capable of resonance energy transfer" Waggoner et.al., which is incorporated herein by reference in it's entirety, including any drawings, discloses complexes comprising a first fluorochrome having first absorption and emission spectra and a second fluorochrome having second absorption and emission spectra. The linker groups between the fluorochromes are alkyl chains. The fluorescent nature of the dyes enables them to be of use in sequencing and nucleic acid detection.

U.S. Pat. No. 5,863,727, entitled "Energy transfer dyes with enhanced fluorescence" Lee et al., which is incorporated herein by reference in its entirety, discloses energy transfer dyes in which the donor and acceptor dyes are separated by a linker between the dyes. The preferred linker between the dyes is 4-aminomethylbenzoic acid (Nucleic Acids Research, 1997, 25(14), 2816–2822). The energy transfer terminators DNA sequencing kit based on this linker is commercially available from Applied Biosystems (Foster City, Calif.) and sold as Big Dye terminator kit.

PCT application WO 00/13026 entitled "Energy Transfer Dyes" Kumar et al., which is incorporated herein by reference in its entirety, including any figures and drawings, discloses energy transfer dyes, their preparation, and their use as labels in biological systems. The dyes are preferably in the form of cassettes, which enable their attachment to a variety of biological materials. The donor dye, acceptor dye and the dideoxynucleoside-5'-triphosphates are all attached to a trifunctional linker, which is based on aromatic aminoacids structure (Tetrahedron Letters, 2000, 41, 8867–8871). The energy transfer terminator kit based on these structures is sold by Amersham Biosciences, Piscataway (N.J.) as DYEnamic ET terminator kit for DNA sequencing.

PCT application WO 01/19841 entitled "Charge-modified nucleic acids terminators" Kumar et al., which is incorporated herein by reference in its entirety, including any figures and drawings, discloses single and energy transfer dye labeled terminators with positive or negative charge(s) incorporated in the linker arm. These terminators are useful in generating DNA sequencing bands free of any 'dye blobs' which are formed by the degradation of dye labeled dideoxynucleoside-5'-triphosphates. The use of charge terminators allows these degradation products to move backward (positive charge terminators) or move ahead of sequence information (negative charge terminators, Finn et.al. Nucleic Acids Research, 2002, 30(13), 2877–2885).

The currently available ET dye terminator sets, generally, suffer from low brightness. This low brightness is due to the inefficiencies in the transfer of the energy absorbed by the donor to the acceptors and re-emission at the emission wavelength of the acceptor. This inefficiency arises because, the structural linkages used to join the donor, the acceptors, and the nucleic acid bases together to form the dye terminators are less than optimal. Therefore, there remains a need for additional improvements in energy transfer dye cassette construction for maximum brightness and attachment to biological molecules.

SUMMARY OF THE INVENTION

The current invention provides energy transfer dyes and labeled nucleotides, which are brighter and are substrates for DNA polymerases. The energy transfer dyes use heterocyclic linker structures, such as piperidine and piperazine as the core molecule, to attach the donor and acceptor dyes. For example, in case of piperidnyl-1,1-amino carboxylic acid, the donor dye is attached to the secondary nitrogen atom and the acceptor dyes are attached to the amino group. The carboxylic acid residue of the molecule is used to attach the biological molecule of interest, such as a nucleoside, nucleotide, oligonucleotide or other biological molecule of interest. The attachment position of donor and acceptor dyes may also be switched.

The current invention also provides a set of four terminators derived from the heterocyclic linkers of this invention. The terminator set include fluorescein (FAM) or rhodamine 110 (R110) as the donor dye and rhodamine 110 (R110), rhodamine 6G (R6G), tetramethylrhodamine (TAMRA) and rhodamine X (ROX) or cyanine dyes as the acceptor dyes. This terminator set is optimized for DNA sequencing. The labeled nucleotide terminators in the kit are brighter than the existing kits and give uniform bands. The method of their preparation and use in DNA sequencing is also disclosed in the present invention.

Disclosed are compositions and methods of making the heterocyclic FRET dyes of this invention and their attachment to the biological molecules of interest such as nucleosides, nucleotides (mono, di, or triphosphates) or oligonucleotides.

The numbers and letters in bold represents the compound numbers given in schemes and in experimental sections.

BRIEF DESCRIPTION OF THE DRAWINGS

FIG. 1 is a general scheme for the synthesis of piperidine linker derived FRET cassettes and labeling dideoxynucleoside-5'-triphosphates FIG. 2 is a plot of signal strength at 800 bases with different concentration of TAMRA labeled ddATP of different linker lengths FIG. 3 shows single color electropherograms of FAM-Phe-TAMRA-11-ddATP (3F), FAM-Piperidine-TAMRA-11-ddATP (7), and FAM-Piperidine-TAMRA-18-ddATP (8) terminated amplicons.

FIG. 4 is a plot of signal strength at 800 bases with different concentration of ROX labeled ddCTP of different linker lengths FIG. 5 shows single color electropherograms of FAM-Phe-ROX-11-ddATP (4F), FAM-Piperidine-ROX-11-ddATP (10), and FAM-Piperidine-ROX-18-ddATP (11) terminated amplicons.

DETAILED DESCRIPTION OF THE INVENTION

The efficiency of FRET depends on a number of factors. According to Forster's theory (Joseph R. Lakowicz, "Principles of Fluorescence Spectroscopy" $2^{nd}$ Edition, Chapter 13, Kluwer Academic Plenum Publishers, New York, Boston, Durdrecht, London, Moscow 1999), the primary factors are:

1) The overlap of the emission spectrum of the donor and the absorption spectrum of the acceptor;
2) The separation, in distance, between the donor and the acceptor; and
3) The spatial orientation between the dipoles of the donor and the acceptor.

In practice, the situation is much more complicated. Specific interactions between the donor and the acceptor, may in cases, lead to quenching with very little emission from the acceptor even when the donor emission is completely absent. Furthermore, the extent to which the donor is quenched has very little bearing on the amount of energy being transferred to the acceptor and, hence, the emission observed. A mathematical treatment to describe the practical ET process associated with these dye-terminators, has now been developed and is further described below. In such a mathematical treatment, three experimentally measurable parameters are of paramount importance:

1) PQEQ (Percentage of quenching of the donor) which is defined as;

$PQEQ=(1-\text{Emission}_{donor\ in\ the\ donor/acceptor\ pair}/\text{Emission}_{same\ amount\ of\ donor\ in\ the\ absence\ of\ the\ acceptor})\times 100\%$, 2) PAEE (Percentage Acceptor Emission Efficiency):

$PAEE=(\text{Emission efficiency of the acceptor in the donor acceptor pair})/(\text{Emission efficiency of the acceptor without the donor})\times 100\%$, and 3) PET (Percentage Energy Transfer),

*PET*=Quantum yield of the donor×[(Emission efficiency of acceptor when excited at the donor excitation wavelength)/(Emission efficiency of the donor in the absence of the acceptor).

PET, as defined, actually becomes the quantum yield of the donor/acceptor pair when excited at the donor excitation wavelength and the emission measured at the acceptor emission wavelength.

The above methodology can be extended to ET assemblies consisting of one donor and more than two acceptors.

Furthermore, from these numbers, a flow diagram can be constructed to show the photon flow throughout the ET process. As an example, the numbers for the set of four ET dye-terminators (Kumar et.al. PCT WO 00/13026; Nampalli et.al., Tetrahedron Letters 2000, 41, 8867) used in current DNA sequencing reactions are given in Table One below.

TABLE ONE (All measurements in 1 × TBE + 8 M urea buffer, 488 nm excitation)

| Compound* | PQEQ | PAEE | PET |
|---|---|---|---|
| FAM-Phe-R110-11-ddGTP (1F) | 92% | Not measurable** | 8% |
| FAM-Phe-R6G-11-ddUTP (2F) | 99% | 47% | 26% |
| FAM-Phe-TAM-11ddATP (3F) | 98% | 48% | 16% |
| FAM-Phe-ROX-11ddCTP (4F) | 99% | 35% | 19% |

*The structures of these compounds are given in FIG. A.
**The emissions from FAM and R110 are not resolvable.

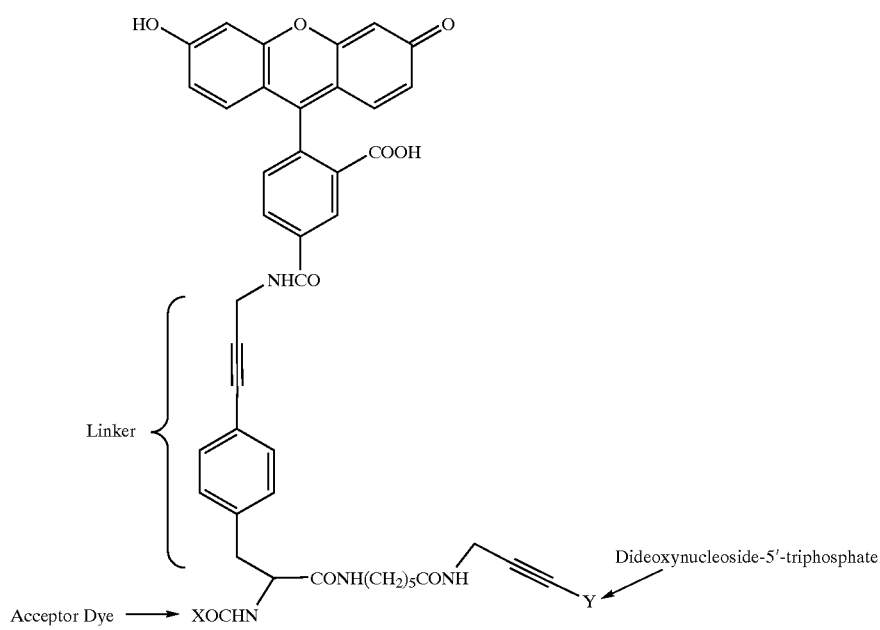

FIG. A

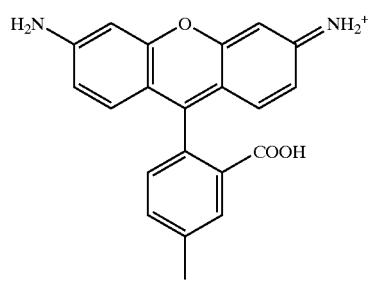

X = 5-Rhodamine 110 (R110)
Y = ddGTP

1F

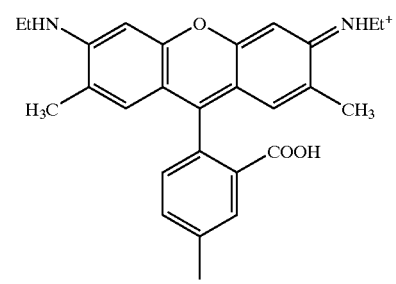

X = 5-Rhodamine 6G (R6G)
Y = ddUTP

2F

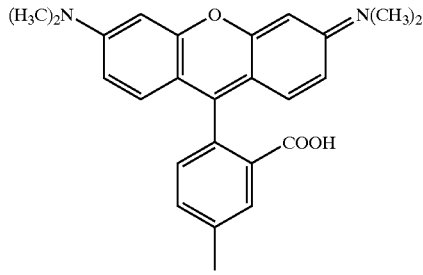

X = Tetramethylrhodamine
(TAMRA or TAM)
Y = ddATP

3F

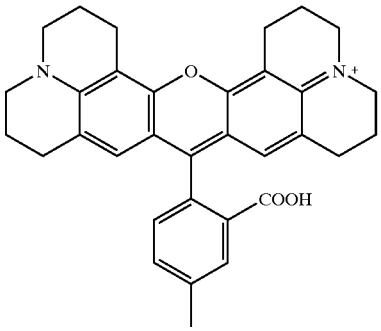

X = Rhodamine-X (ROX)
Y = ddCTP

2F

As an illustration, a photon flow diagram can be constructed using the compound (4F) as an example.

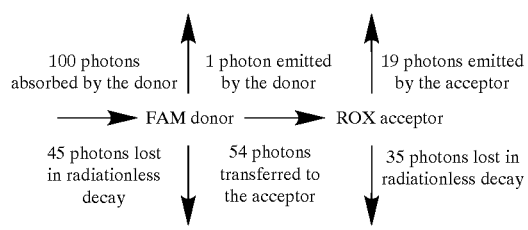

The construction of the above diagram is relatively simple. Since PQEQ for the compound (4F) is equal to 99%, only one photon in 100 photon absorbed by the donor (FAM) is re-emitted by the donor. We have PET equals to 0.19, it means that for the 100 photons absorbed by the donor, 19 photons are emitted by the acceptor (ROX). Since the PAEE is 0.35, and assuming that the quantum yield of ROX in its free state is 1.0 relative to FAM, we need the input of 19/0.35 or 54 photons to have 19 photons emitted by ROX acceptor. It follows that the number of photons lost by the acceptor (ROX) in processes other than fluorescence must be 35 (54−19). Then, from the conservation of photons, the number of photons lost in radiationless processes from the donor FAM should be 45 (100−1−54).

During our extensive search for improved brightness of dye terminator sets over those listed in Table One, we discovered a novel type of ET dyes based on piperidinyl-1, 1-amino carboxylic acid. The ring nitrogen (NH) of the piperidine nucleus is used to attach the donor dye (fluorescein). The amino group at the 1 position of the piperidine is used to attach the acceptor dyes (Rhodamine 110, Rhodamine 6G, Tetramethyl rhodamine, Rhodamine-X, Cy 5 etc.) and the biological molecule such as nucleoside triphosphates, oligonucleotides, proteins is attached to the activated carboxylic acid. The ET dye cassettes and terminators derived from this architecture are brighter and the dideoxy nucleotides are good substrate for DNA polymerases Thus this invention provides energy transfer dyes of the formula:

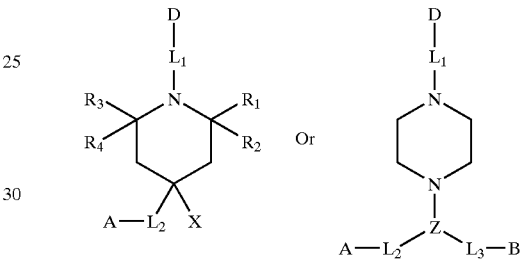

wherein

D is a donor dye selected from the group consisting of xanthine dyes, rhodamine dyes, and cyanine dyes;

$L_1$ is a functional group selected from the group consisting of H, $C_1$–$C_{20}$ alkynylamine, alkynol, alkenamine, alkylamine, keto, and thiol, through which D is covalently attached;

$R_1$, $R_2$, $R_3$ and $R_4$ independently represent H, alkyl, halo, hydroxy, thio, nitro, amino or alkylamino groups;

$L_2$ is an amine selected from the group consisting of $C_1$–$C_{20}$ alkynylamine, alkynol, alkenamine, alkylamine, keto, and thiol, through which A is covalently attached;

X is an aldehyde, an acid, an acid chloride, an ester, hydroxymethyl, $CH_2O$-mesylate, $CH_2O$-triflate, mercaptomethylene, phosphoramidite or other reactive groups capable of forming a covalent bond with amine, thiol, hydroxy, or haloacetyl containing biological molecules; or X=$L_3$B wherein, $L_3$ is a functional group consisting of carboxylic acid, N-hydroxy-succinimidyl ester, acid chloride, maleimide, hydrazide, or sulfonyl chloride, capable of forming a covalent bond with biological molecule, B B is a biological molecule selected from the groups consisting of nucleosides, nucleoside-monophosphate, diphosphate, or triphosphates, thiophosphates, alkenyl or alkynylamino substituted dideoxynucleoside triphosphates, deoxynucleoside triphosphates, nucleoside triphosphates, amino acids, proteins, or modified oligonucleotides;

A is an acceptor dye selected from the group consisting of xanthine dyes, rhodamine dyes and cyanine dyes;

wherein the positions of A and D are interchangeable.

In another embodiment the present invention provide the energy transfer dye cassettes and the corresponding dideoxynucleoside-5'-triphosphates of the following structures, their preparation and use in DNA sequencing.

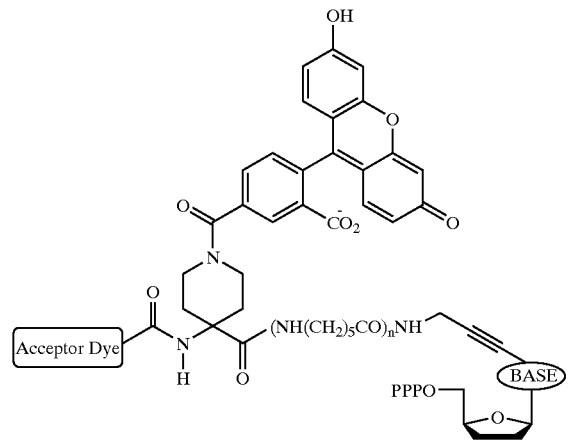

Wherein
Acceptor dye is selected from xanthine class of dyes, rhodamine dyes, or cyanine dyes BASE is selected from cytosine, thymine, uracil, adenine, guanine, hypoxanthine, 2,6-diaminopurine, 2-aminopurine, 7-deazapurines, 7-deaza-8-azapurines, and other modified heterocyclic bases, and n is 0–3.
The acceptor dye and the donor dye may be attached interchangeably at either of the ring nitrogen or the primary amino group of the piperidine 1,1-amino carboxylic acid.
The ET dye cassettes for labeling can also be generated from the other similar heterocyclic aminoacids, examples of which are shown below.

EXAMPLES OF OTHER HETEROCYCLE DERIVED FRET SYSTEMS

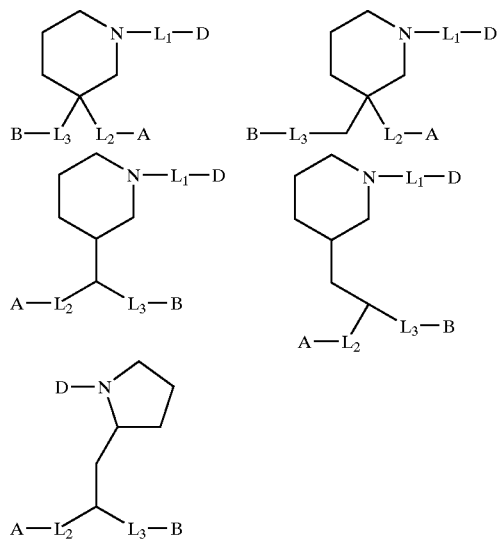

In all the heterocycle derived FRET cassettes, the donor dyes (D) comprise the 5 and 6-regioisomers of the following: carboxyfluorescein (FAM), Cy3, rhodamine green (R110) and the acceptor dyes (A) comprise the 5 and 6-regioisomers of the following: 5-carboxyrhodamine (R110), 6-carboxyrhodamine, 5-carboxyrhodamine-6-G (R6G or REG), 6-carboxyrhodamine-6-G,N,N,N',N'-tetramethyl-5-carboxyrhodamine (TAMRA),N,N,N',N'-tetramethyl-6-carboxyrhodamine, 5-carboxy-X-rhodamine (ROX), 6-carboxy-X-rhodamine, 1-(ε-carboxypentyl)-1'-ethyl-3,3,3',3'-tetramethyl-5, 5'-disulphonato-carbocyanine (Cy3), 1-(ε-carboxypentyl)-1'-ethyl-3,3,3',3'-tetramethyl-4,5,4',5'-(1,3-disulphonato)dibenzo-carbocyanine (Cy3.5), 1-(ε-carboxypentyl)-1'-ethyl-3,3,3',3'-tetramethyl-5,5'-disulphonato)dibenzodicarbocyanine (Cy5), 1-(ε-carboxypentyl)-1'-ethyl-3,3,3',3'-tetramethyl-4,5,4',5'-(1,3-disulphonato)dibenzo-dicarbocyanine (Cy5.5), 1-(ε-carboxypentyl)-1'-ethyl-3,3 and 3',3'-tetramethyl-5,5'-(1,3-disulphonato)tricarbocyanine (Cy7) or related dyes and wherein acceptor dye, A is capable of accepting energy from the donor dye, D.

FAM, R110, REG, TAMRA, and ROX are trademarks of Applied Biosciences (Foster City, Calif.), Cy3, Cy3.5, Cy5, Cy5.5, and Cy7 are trademarks of Amersham Biosciences (Piscataway, N.J.)

Additionally, the present invention includes the FRET cassettes (vide supra), which have a nitrogen atom in the ring systems, a 1,2- or 1,3-related attachment to A and B. Note that these systems possess one or two chiral centers, which influence the relative orientation of A, B and D, thereby influencing the energy transfer efficiencies (brightness or quantum yield).

A number of single dye labeled terminators with different linkers between the dye and the dideoxynucleoside-5'-triphosphates were synthesized and their brightness (PET) was measured by excitation at 488 nm. The brightness of single dye labeled terminators was also compared with energy transfer dye labeled terminators of the present invention and terminators previously disclosed. The synthesis of piperidine derived terminators was undertaken as shown in FIG. 1. Thus, as can be seen in Example 1, N-FMOC-piperidinyl-1,1-amino carboxylic acid (1) was reacted with the protected fluorescein-5-carboxylic acid chloride (3) to give the fluorescein labeled piperidinyl-1,1-amino carboxylic acid (4). The acceptor dyes (in the form of NHS esters) were attached to the amino group after deprotection with piperidine. Finally, the activation of acid to the corresponding active ester followed by reaction with appropriately linked propargylamino-ddNTPs provided the piperidine linker derived energy transfer dye terminators. Alternatively, N-t-Boc-piperidinyl-1,1-carboxylic acid methyl ester can be used to synthesize single and ET dye cassettes of the present invention.

The energy transfer efficiency (PET) was measured for all the single dye labeled dideoxynucteoside-5'-triphosphates (terminators) and the energy transfer terminators synthesized in this invention. All the dye terminators were excited at 488 nm and emission was measured at their respective emission wavelengths. The results are provided in Table 2, below.

TABLE 2

(All measurements in 1 × TBE + 8 M urea buffer, 488 nm excitation)

| Dye terminator | PET |
|---|---|
| FAM-18-ddGTP (I) | 38* |
| R110-18-ddGTP (II) | 28* |
| R6G-11-ddUTP (III) | 28* |
| TAMRA-11-ddATP (IV) | 1* |
| ROX-11-ddCTP (V) | 1* |
| FAM-piperidine-TAMRA-11-ddATP (7) | 21 |

TABLE 2-continued (All measurements in 1 × TBE + 8 M urea buffer, 488 nm excitation)

| Dye terminator | PET |
| --- | --- |
| FAM-piperidine-TAMRA-18-ddATP (8) | 41 |
| FAM-piperidine-ROX-11-ddCTP (10) | 40 |
| FAM-piperidine-ROX-18-ddCTP (11) | 60 |

*For single dye terminators, PET equivalent = quantum yield of the Single dye-terminator × (extinction coefficient at 488 nm)/(extinction coefficient at absorption maximum).
**Emission from the R110 can not be resolved from that of FAM.

The molecular structures of the dye terminators listed in TABLE 2 are given below.

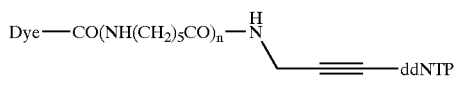

I: Dye=FAM, n=2, ddNTP=ddGTP
II: Dye=R110, n=2, ddNTP=ddGTP
III: Dye=R6G, n=1, ddNTP=ddUTP
IV: Dye=TAMRA, n=1, ddNTP=ddATP
V: Dye=ROX, n=1, ddNTP=ddCTP

Structures of Single Dye Labeled dideoxynucleoside-5'-triphosphates (Terminators)

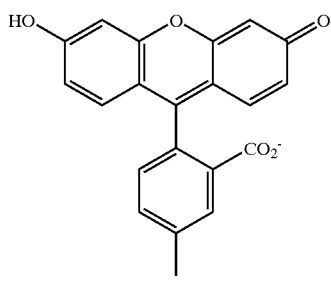

FAM

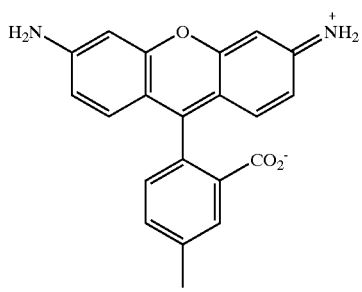

R110

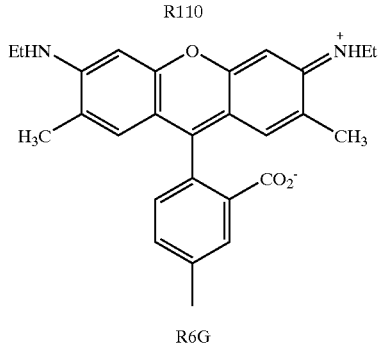

R6G

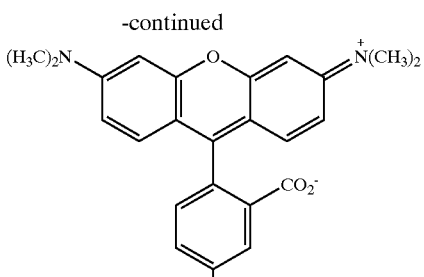

TAMRA

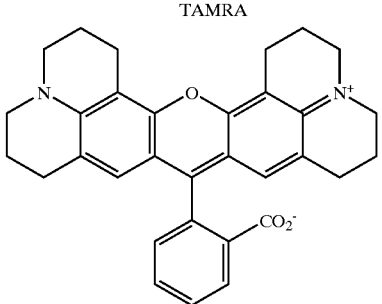

ROX

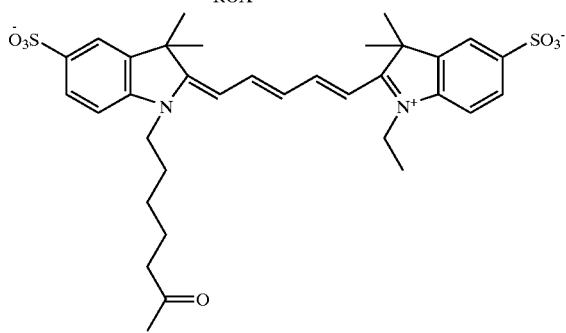

Cy5

The single dye labeled terminators and energy transfer dyes labeled terminators of this invention (described above) were tested in DNA sequencing reactions using thermostable DNA polymerase. The utility of individual dye labeled terminator was ascertained based on the overall sequence quality, brightness, and uniformity of the bands. Based on these criterions, a new set of dye-terminators was constructed. The PET of terminators of this new set is given below.

| Dye-terminator | PET or equivalent | DYEnamic ET set |
| --- | --- | --- |
| FAM-18-ddGTP (IX), | 38 | 8 (1F) |
| R6G-11-ddUTP (XI), | 28 | 26 (2F) |
| FAM-piperidine-TAM-18-ddATP (8), | 41 | 16 (3F) |
| FAM-piperidine-ROX-18-ddCTP (11) | 60 | 19 (4F) |

The invention also includes a reagent and a method for making the reagent including incubating the fluorescent water-soluble labeling complex described above with a carrier material. The complex or the carrier material having a functional group that will react with a reactive group of the other of the complex or the carrier to form a covalent bond between them. The carrier material can be selected from the group consisting of polymer particles, glass beads, cells, antibodies, antigens, proteins, enzymes, and nucleotides derivatized to contain one of an amino, sulfhydryl, carbonyl, carboxyl, or hydroxyl groups. Alternatively, the carrier material may contain the reactive groups and the fluorescent labeling complex of the invention may contain any of the aforementioned functional groups that will react with the reactive group to form covalent bonds.

In an alternative embodiment, the fluorescent complexes of the invention need not have a reactive group when used to non-covalently bind to another compound. For example, the complex may be dissolved, then mixed in an organic solvent with a polymer particle, such as polystyrene and then stirred by emulsion polymerization. The solvent is evaporated and the fluorescent dye complex is absorbed into the polystyrene particles.

The invention is further described by reference to the following examples. These examples are provided for illustration purposes only and should not be construed as limiting the appended claims and the scope of the invention. The current invention should encompass any and all variations that become evident from the teachings provided herein. Numbers that appear in bold below refer to the various numbered compounds in the synthesis.

Example 1

Synthesis of Piperidine Linker Derived Terminators
(FAM-Piperidine-ROX-X-ddNTPs)

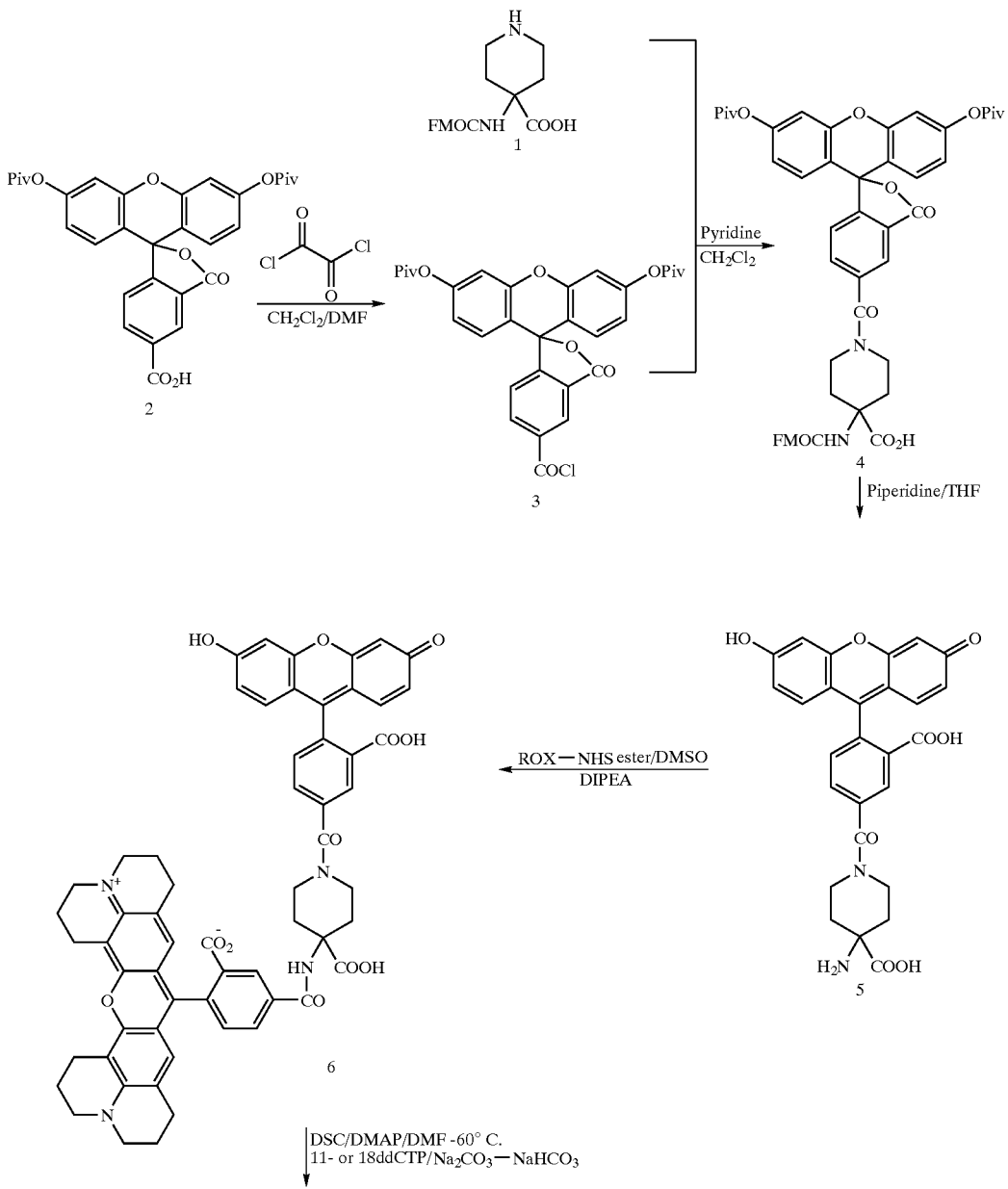

-continued

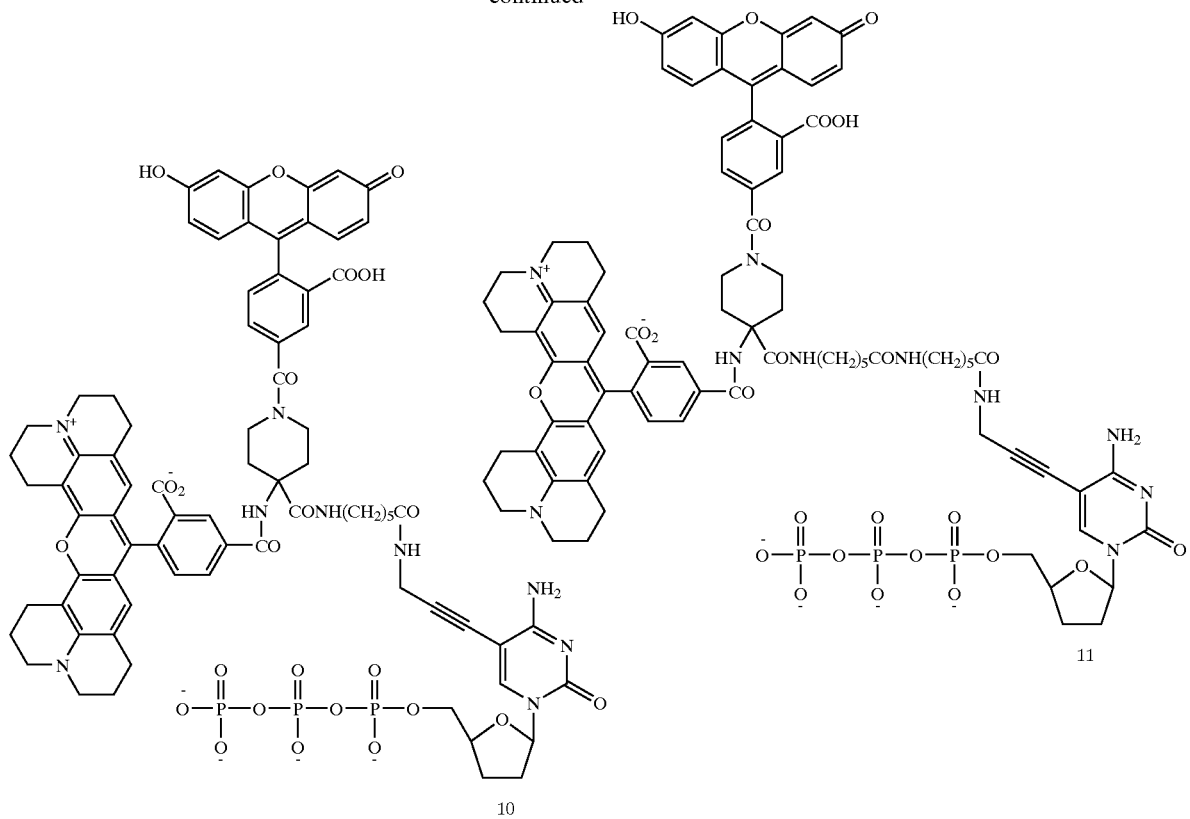

10

11

4-N-(dipivaloylfluorescein-5-carbonyl)-N-FMOC-piperidinyl-1,1-amino carboxylic acid (4)

N-FMOC-piperidinyl-1,1-amino carboxylic acid 1 (0.4 g, 1.0 mmol) was dried by coevaporation with anhydrous pyridine (10 ml). The dried substrate was dissolved in a mixture of methylene chloride (5 ml) and pyridine (5 ml). The reaction flask was cooled in an ice bath and a solution of dipivaloyl-5-carboxyfluorescein acid chloride 3 (1.25 mmol, prepared by treating dipivaloyl-5-carboxyfluorescein 2 with oxalyl chloride in methylene chloride in the presence of DMF) in methylene chloride (10 ml) was added. The reaction mixture was stirred at 0–5° C. for 2 h and allowed to warm to room temperature. The reaction was continued overnight and quenched by the addition of water (0.5 ml). The reaction mixture was diluted with chloroform (100 ml) and washed with water (50 ml). Organic layer was dried (sodium sulfate) and evaporated. The residue was coevaporated with toluene and purified by silica gel column chromatography using a gradient of 0–5% methanol in methylene chloride as the eluent.

4-N-(fluorescein-5-carbonyl)piperidinyl-1,1-amino carboxylic acid (5)

To a solution of compound 4 (150 mg) in THF (15 ml) piperidine (5 ml) was added and the mixture was stirred at room temperature for 18 h. The reaction mixture was evaporated to dryness and the residue was purified by column chromatography using a gradient of 0–100% methanol in methylene chloride as the eluent.

4-N-(fluorescein-5-carbonyl)-N-ROX-piperidinyl-1,1-amino carboxylic acid (6)

A mixture of the compound 5 (20 mg) and ROX-NHS ester was dried by coevaporation with dry DMF (15 ml). Then it was dissolved in anhydrous DMSO (5 ml) to which N,N-diisopropylethyl amine (0.5 ml) was added and the reaction mixture was stirred at room temperature for 6.5 h. The reaction mixture was loaded on a silica gel column, which was packed in methylene chloride. The product was eluted utilizing 0–100% methanol in methylene chloride followed by 1%-trifluoroacetic acid in methanol. The fractions containing the product were evaporated and the residue was coevaporated with toluene. The residue was further purified on a Q-Sepharose column. Eluent: 0.1 N triethylammonium bicarbonate containing 40% acetonitrile to 1N triethylammonium bicarbonate containing 40% acetonitrile. The fractions containing the product were collected and evaporated to give 6.

5-FAM-piperidine-ROX-11-ddCTP (10).

Compound 6 (10 mg, 0.01 mmol) was dried by coevaporation with dry DMF (8 ml). Then it was dissolved in dry DMF (3 ml) to which a solution of disuccinimidyl carbonate (18 mg) in DMF (1 ml) was added. The reaction flask was cooled to −60 ° C. and a solution of DMAP (9 mg) in DMF (1 ml) was added dropwise. After 10 min the reaction mixture was allowed to warm to −30° C. and a solution of 11-ddCTP (0.3 mmol) in pH 9.5 $NaHCO_3/Na_2CO_3$ buffer (8 ml) was added. The reaction mixture was allowed to warm to room temperature and the reaction continued for 3 h. The reaction mixture was directly loaded on a silica gel column, which was packed in 50% methanol-chloroform. The column was washed with methanol and the product was eluted using a mixture of isopropanol, ammonium hydroxide and water (6:3:1). The fractions containing the product were collected and evaporated to a small volume, filtered through 0.4 μ filter and loaded on a Q-sepharose column. The product was eluted with a gradient of 0.1N triethylammonium bicarbonate containing 40% acetonitrile to 1 N triethylammonium bicarbonate containing 40% acetonitrile. The appropriate fractions containing the pure product were collected and evaporated. The residue was coevaporated with methanol (5×30 ml) to afford compound 10.

5-FAM-Piperidinyl-ROX-18-ddCTP (11)

FAM-piperidinyl-ROX, the ET cassette 6 (4 mg 0.004 mmol) was dissolved in anhydrous DMF(2 ml). A total of 8 mg (0.03 mmol, 8 eq) DSC was added. The mixture was stirred and cooled to −60 °C., at this temperature, an anhydrous DMF solution (1 mL) of DSC (2.4 mg was added dropwise. After 15 minutes TLC indicated complete conversion to the NHS ester. The reaction mixture was warmed up to −30° C. and a buffer (0.1 M $Na_2CO_3$—$NaHCO_3$; pH 8.5) solution of 18-ddCTP (1 eq) was added. Then, the reaction mixture was allowed to warm up to room temperature and stirred for another 3 hours. The desired product 11 was purified on a Q-Sepharose column as described for 10.

Example 2

Synthesis of FAM-Piperidine-TAMRA-X-ddNTPs

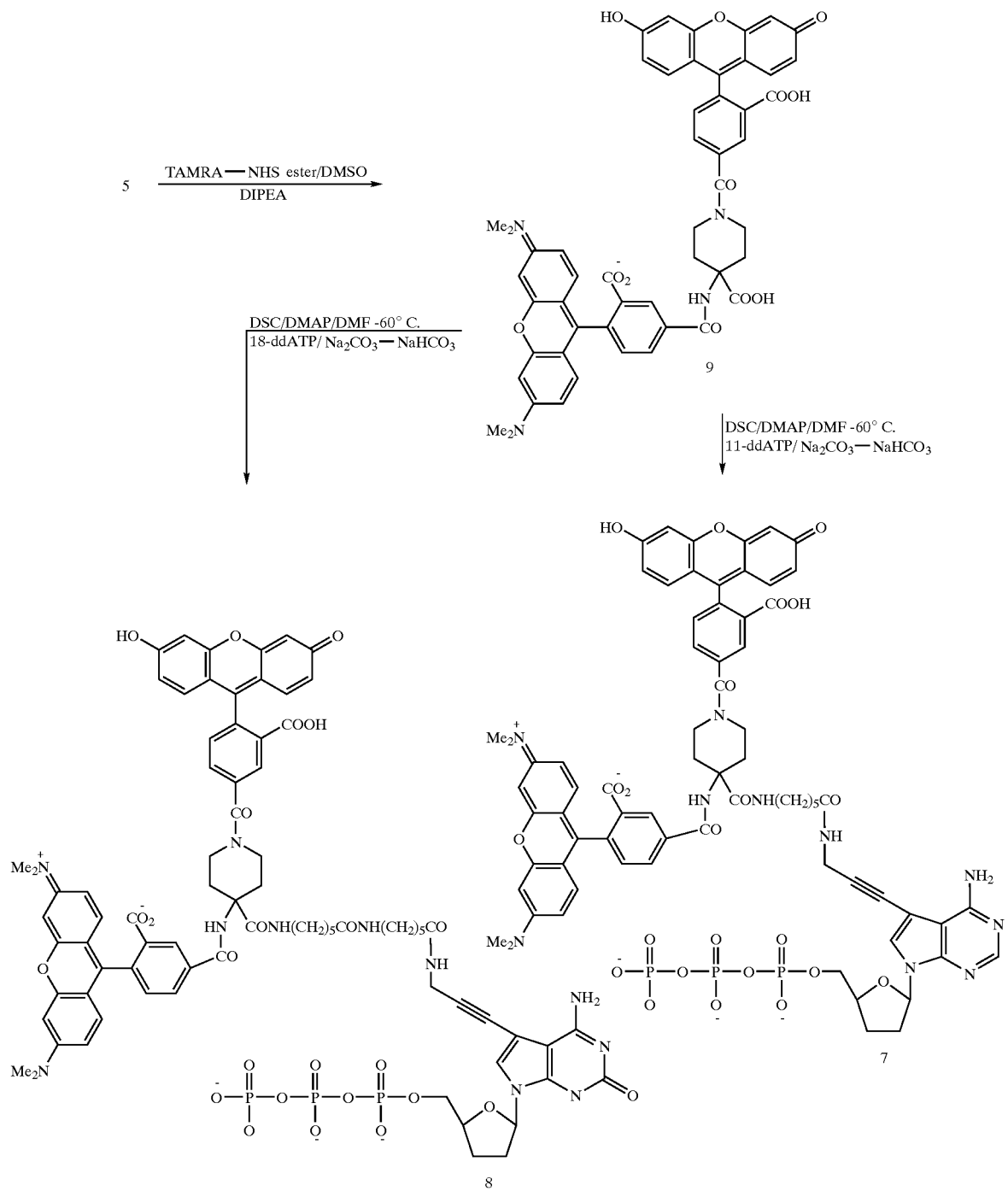

4-N-(fluorescein-5-carbonyl)-N⁴-TAMRA-piperidinyl-1,1-amino carboxylic acid (9)

Compound 5 (24 mg, 0.048 mmol) was dissolved in anhydrous DMSO (5 mL) and to the stirred solution at room temperature was added DIPEA (0.1 mL, 0.58 mmol, 12 eq) followed by TAMRA-NHS ester (30 mg, 0.57 mmol, 1.2 eq). The reaction mixture was stirred overnight and the desired product 9 (60%) was isolated using a Q-Sepharose column as described for compound 6.

5-FAM-Piperidinyl-TAMRA-11-ddATP (7) and 5-FAM-Piperidinyl-TAMRA-18-ddATP (8)

Compounds 7 and 8 were synthesized from 9 on a 3.8 μmole scale using 8 equivalents of DSC, 5 equivalents of DMAP and 1 equivalent of 11- or 18-ddATP following similar reaction conditions described for 10.

Example 3

Synthesis of FAM-Piperidine-R110-X-ddNTP and FAM-Piperidine-R6G-X-ddNTP

5-FAM-Piperidinyl-R110-11-ddGTP (15)

Terminator 15 was synthesized and purified from 5 via 14 following the procedure similar to that of 7.

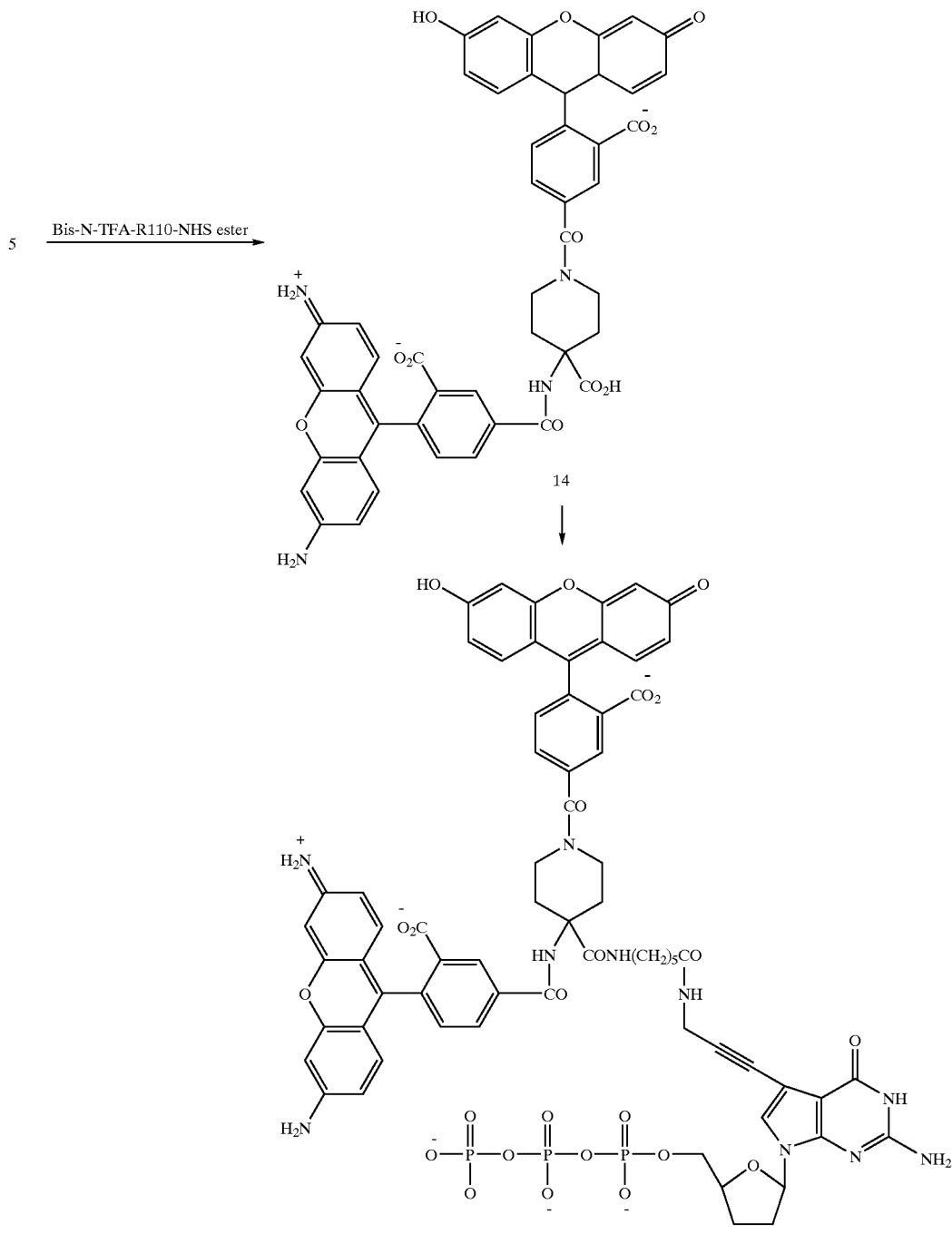

Example 4

Synthesis of a single dye (R110 as the donor dye) cassette derived from Piperidine Piperidinyl-R110 Cassette Synthesis (19)

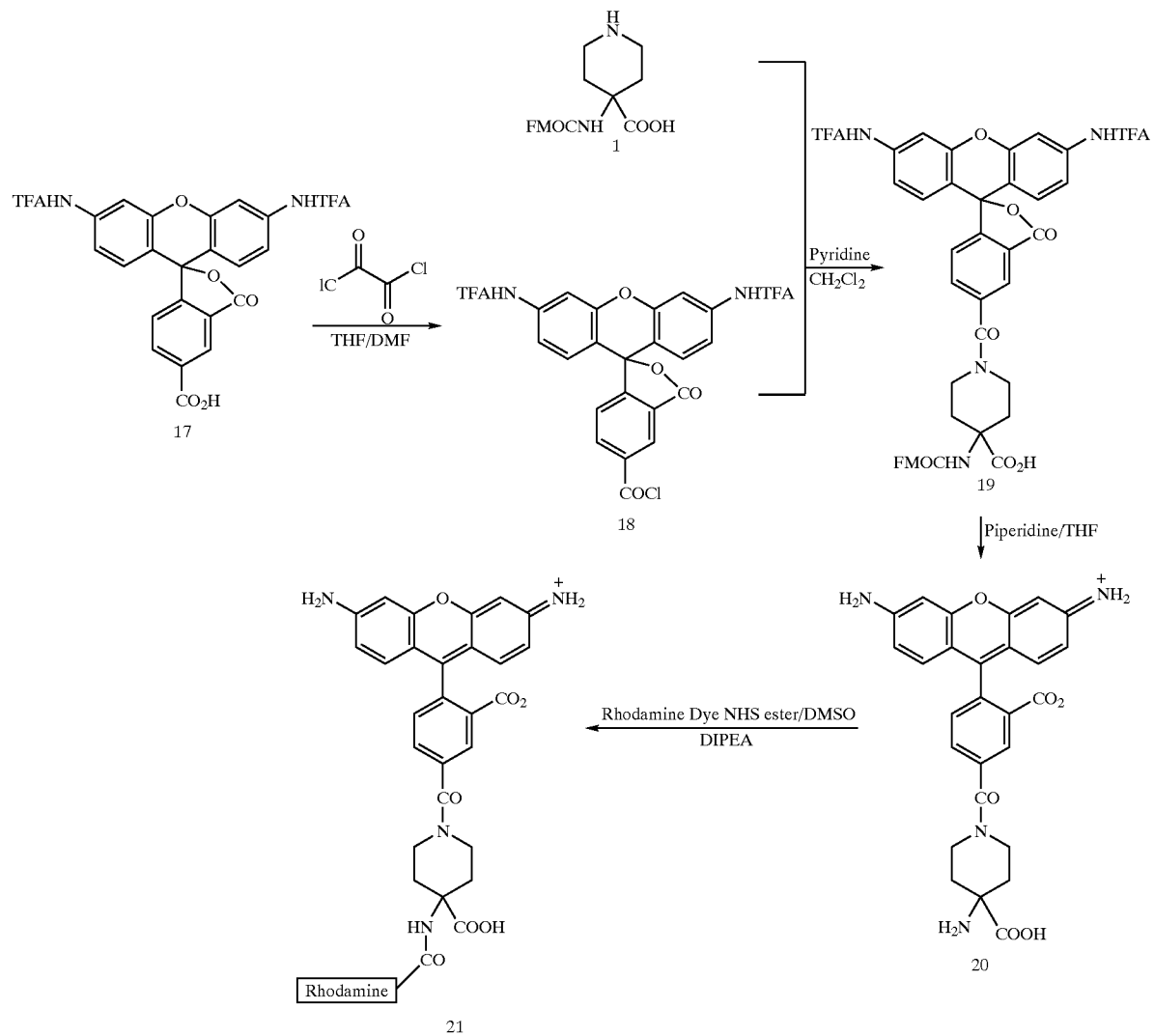

TFA-5-R110 acid 17 (0.2 g, 0.35 mmol) was dried by coevaporation with dry DMF (10 ml). The dry material was dissolved in anhydrous THF (6 ml). The reaction flask was cooled in ice bath and a drop of DMF followed by oxalyl chloride (0.25 ml, 0.5 mmol) was added in over 5 min time. The reaction was continued for 15 min in ice bath and then allowed to warm to room temperature. After 2 h at room temperature evaporated to dryness, coevaporated with dry methylene chloride (10 ml) and dried under high vacuum for 1.5 h to provide 18.

FMOC-piperidine 1 derivative (0.14 g) was dried by coevaporation with dry pyridine (10 ml). Then it was dissolved in pyridine (3 ml) to which a solution of acid chloride (18) in a mixture of methylene chloride (5 ml) and anhydrous acetonitrile (1 ml) was added dropwise at 0° C. The reaction mixture was stirred at 0° C. for 3 h and allowed to warm to room temperature. After stirring the reaction mixture at room temperature for 15 h, the reaction was quenched by the addition of water (1 ml). The reaction mixture was diluted with methylene chloride and washed with water. Organic layer was dried (sodium sulfate), evaporated and coevaporated with toluene. Finally the product was purified by silica gel column chromatography using 0–8% methanol-methylene chloride as the eluent. The appropriate fractions containing the desired product were pooled and evaporated to give 19. Compound 19 can be converted to 21 via 20 for the generation of R110-Piperidine-Rhodamine ET cassette and its corresponding terminators.

The efficiency of FRET in terms of percent energy transfer (PET) was measured between the fluorescein and rhodamine dyes of the heterocyclic FRET-cassettes and terminators on a fluorimeter (Photon Technology International) in 1×TBE, 8 M Urea and compared with the single-dye labelled-terminators. It is clear from the plotted bar graph that the FRET cassettes and terminators of the present invention showed increased PET. The longer spacer terminator (11) displayed 55 times enhanced PET than that of ROX-11-ddCTP (single-dye labelled-terminator) and 3.2 times than that of commercial 4F, while the shorter spacer terminator (10) showed 2.1 times enhanced PET over 4F. The next terminator, FAM-Piepridine-TMR-18-ddATP (8), whose fluorescence enhancement is also desirable as it is far removed in the spectrum for overlapping with its absorption, showed 41 times increased PET over the single-dye labelled-terminator and 2.5 times over the commercial 4F.

Synthesis of FAM-Piperidine-Cy5-X-ddNTPs

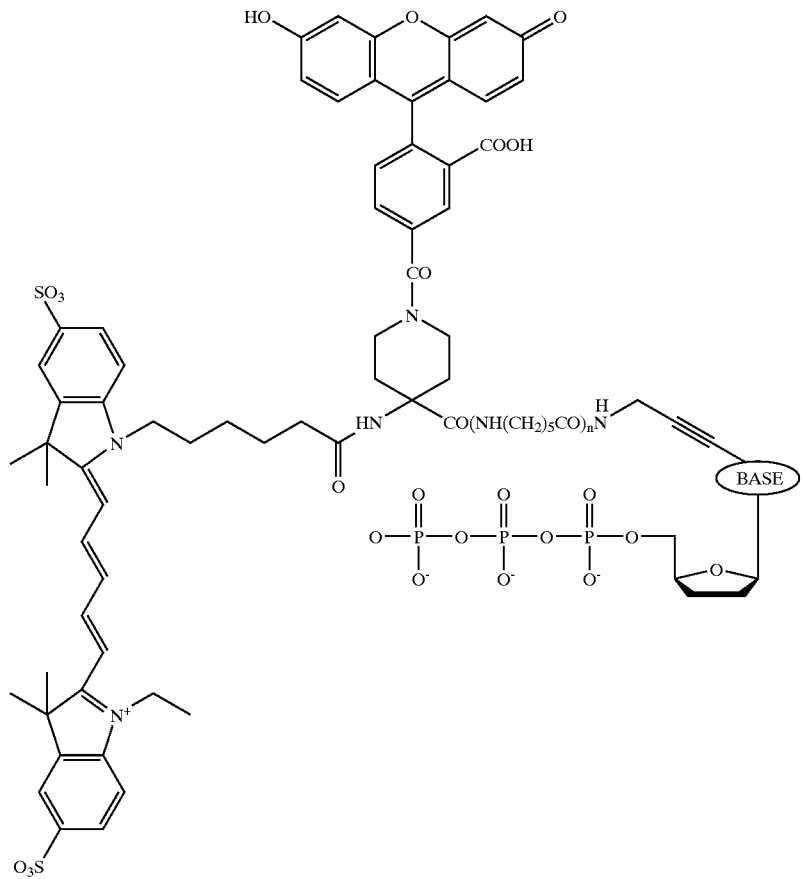

The synthesis of energy transfer terminators with Cy5 as an acceptor dye can be carried out exactly the same way as given in example 1 and 2. Cy5 NHS ester is used in place of rhodamine-NHS ester.

Example 5

Sequencing DNA Using Single and Energy Transfer Dye Labeled Dideoxynucleoside Triphosphates A sequence of M13mp 18 template DNA was generated using standard "−40" primer. The reaction mixture (20 μl) contained 200 μM each of dATP, dCTP, and dTTP, 1000 μM dITP, 160 nM FAM-18-ddGTP, 125 nM R6G-11-ddUTP, 95 nM FAM-Piperidine-TMR-18-ddATP, 60 nM FAM-Piperidine-ROX-18-ddCTP, 2 pmol −40 primer, 200 ng M13mp 18 DNA, 20 units of Thermo Sequenase or other mutated DNA polymerase (Amersham Biosciences), 0.0008 units *Thermoplasma acidophilum* inorganic pyrophosphatase, 50 mM Tris-HCl pH 8.5, 35 mM KCl and 5 mM $MgCl_2$.

The reaction mixture was incubated in a thermal cycler for 25 cycles of 95° C., 20 Sec; 50° C., 30 Sec., and 60° C., 120 Sec. After cycling, the reaction products were precipitated with ethanol using standard procedures, washed and resuspended in formamide loading buffer. The sample was loaded on an Applied Biosystems model 377 instrument or MegaBACE 1000 (Amersham Biosciences) and results were analyzed using standard software methods.

Those skilled in the art having the benefit of the teachings of the present invention as set forth above, can effect numerous modifications thereto. These modifications are to be construed as being encompassed within the scope of the present invention as set forth in the appended claims.

What is claimed is:

1. An energy transfer dye labeled cassette of the formula:

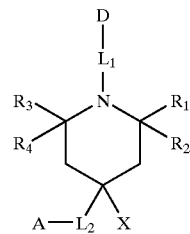

wherein
D is a donor dye selected from the group consisting of xanthine dyes, rhodamine dyes, and cyanine dyes;
$L_1$ is a functional group selected from the group consisting of $C_1$–$C_{20}$ alkynyl-amine, alkynol, alkenamine, alkylamine, keto, and thiol, through which D is covalently attached;

$R_1$, $R_2$, $R_3$ and $R_4$ independently represent H, alkyl, halo, hydroxy, thio, nitro, amino or alkylamino groups;

$L_2$ is an amine selected from the group consisting of $C_1$–$C_2$alkynylamine, alkynol, alkenamine, alkylamine, keto, and thiol, through which A is covalently attached;

X is an aldehyde, an acid, an acid chloride, an ester, hydroxymethyl, $CH_2O$-mesylate, $CH_2O$-triflate, mercaptomethylene, phosphoramidite or other reactive groups capable of forming a covalent bond with amine, thiol, hydroxy, or haloacetyl containing biological molecules;

A is an acceptor dye selected from the group consisting of xanthine dyes, rhodamine dyes and cyanine dyes;

and wherein the positions of A and D are interchangeable.

2. An energy transfer dye labeled compound of the formula:

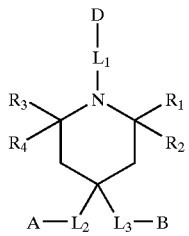

wherein

D, $L_1$, $L_2$, $R_1$, $R_2$, $R_3$, $R_4$, and A are defined as in claim 1;

$L_3$ is a functional group consisting of carboxylic acid, N-hydroxy-succinimidyl ester, acid chloride, maleimide, hydrazide, or sulfonyl chloride, capable of forming a covalent bond with biological molecule, B;

B is a biological molecule selected from the groups consisting of nucleosides, nucleoside-monophosphate, diphosphate, or triphosphates, thiophosphates, alkenyl or alkynylamino substituted dideoxynucleoside triphosphates, deoxynucleoside triphosphates, nucleoside triphosphates, amino acids, proteins, or oligonucleotides;

and wherein the positions of A and D are interchangeable.

3. An energy transfer dye and dye labeled compound of the formula:

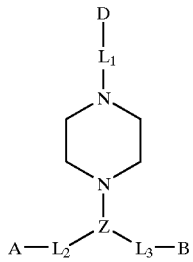

wherein

D, $L_1$, $L_2$, A, $L_3$, and B are defined as in claim 2;

Z is H, alkylene, alkyl, aryl or combination there of;

and wherein the positions of A and D are interchangeable.

4. The energy transfer dye labeled compound of claim 2 or 3 wherein B is alkenyl or alkynylamino substituted nucleoside triphosphate or an oligonucleotide.

5. The energy transfer dye labeled compound of claim 2 or 3 wherein B is a alkenyl or alkynylamino substituted dideoxynucleoside-5'-triphosphate.

6. The energy transfer dye labeled compound of claim 2 or 3, wherein $L_3$ is attached to the C-5 position of pyrimidines and at the C-7 position of 7-deazapurines through a alkynyl, alkenyl or saturated side chain.

7. The energy transfer dye labeled compound of any of claims 1, 2 or 3, wherein said D and A are selected from the group consisting of 5-carboxyrhodamine, 6-carboxyrhodamine, 5-carboxyrhodamine-6-G, 6-carboxyrhodamine-6-G, N,N,N',N'-tetramethyl-5-carboxyrhodamine, N,N,N',N'-tetramethyl-6-carboxyrhodamine, 5-carboxy-X-rhodamine, 6-carboxy-X-rhodamine, 1-(ε-carboxypentyl)-1'-ethyl-3,3,3',3'-tetramethyl-5,5'-disulphonato-carbocyanine, 1-(ε-carboxypentyl)-1'-ethyl-3,3,3',3'-tetramethyl-4,5,4',5'-(1,3-disulphonato)dibenzo-carbocyanine, 1-(ε-carboxypentyl)-1'-ethyl-3,3,3',3'-tetramethyl-5,5'-disulphonato)dibenzo-dicarbocyanine, 1-(ε-carboxypentyl)-1'-ethyl-3,3,3',3'-tetramethyl-4,5,4',5'-(1,3-disulphonato)dibenzo-dicarbocyanine, 1-(ε-carboxypentyl)-1'-ethyl-3,3 and 3',3'-tetramethyl-5, 5'-(1,3-disulphonato)tricarbocyanine or related dyes and wherein acceptor dye, A is capable of accepting energy from the donor dye, D.

8. A method for determining the nucleotide base sequence of a DNA molecule comprising:

incubating a DNA molecule annealed with a primer molecule able to hybridize said DNA molecule in a vessel containing a thermostable DNA polymerase, a compound according to claim 2 or 3; and separating DNA products of the incubating reaction according to size whereby at least a part of the nucleotide base sequence of said DNA molecule can be determined.

9. A kit for DNA analysis comprising a compound of claim 2 or 3 and a DNA polymerase.

10. A compound of the formula

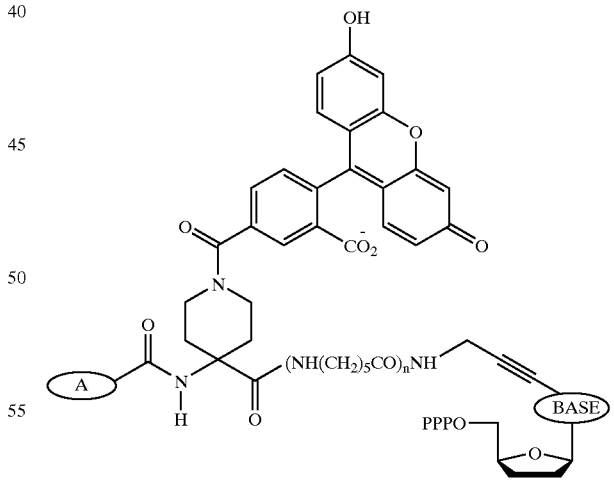

wherein

A is an acceptor dye according to claim 1 above, and

BASE is selected from the group consisting of cytosine, thymine, uracil, adenine, guanine, hypoxanthine, xanthine, 2,6-diaminopurine, 2-aminopurine, 7-deazapurines, 7-deaza-8-azapurines, and homologs thereof, and n is 0–3.

11. A kit for DNA sequencing comprising a compound of claim 10.

12. A kit according to claim 11, further comprising a DNA polymerase.

13. A deoxyribonucleic acid sequence comprising one or more compounds of claim 10 in monophosphate form.

14. Method of determining the nucleotide base sequence of a DNA molecule comprising:
   a) incubating a DNA molecule annealed with a primer molecule able to hybridize to said DNA molecule in a vessel containing a thermostable DNA polymerase, a compound of claim 10; and
   b) separating DNA products of the incubating reaction according to size whereby at least a part of the nucleotide base sequence of said DNA molecule can be determined.

15. A compound according to claim 10 of the formula

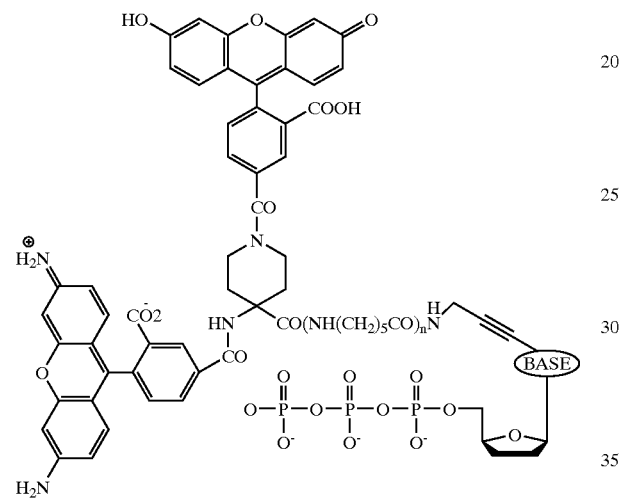

wherein

BASE is selected from the group consisting of adenine, 7-deaza-adenine, guanine, 7-deaza-guanine, uracil, cytosine, hypoxanthine and 7-deaza-hypoxanthine.

16. A compound according to claim 10 of the formula

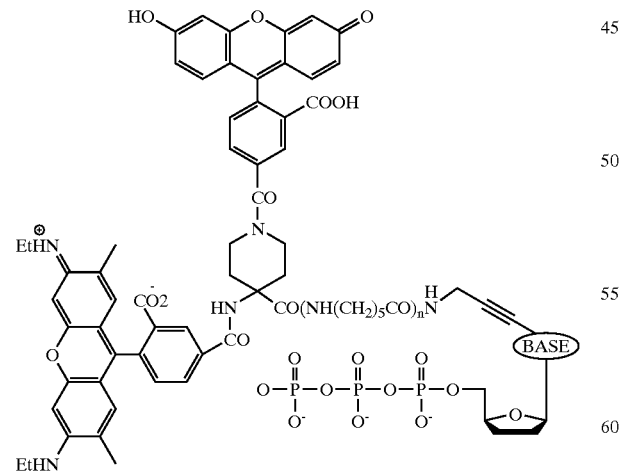

wherein

BASE is selected from the group consisting of adenine, 7-deaza-adenine, guanine, 7-deaza-guanine, uracil, cytosine, hypoxanthine and 7-deaza-hypoxanthine.

17. A compound according to claim 10 of the formula

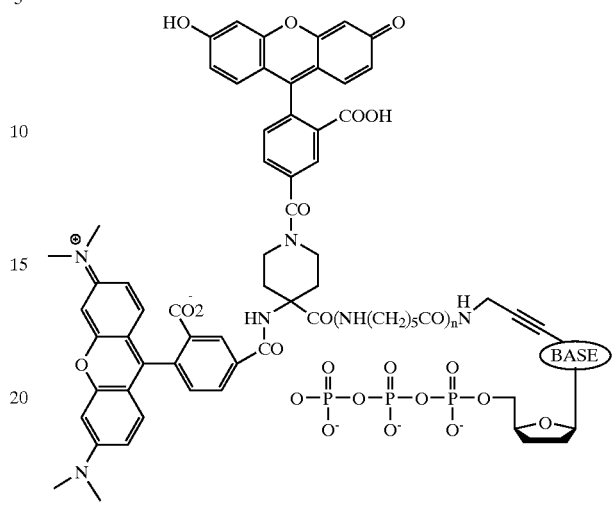

wherein

BASE is selected from the group consisting of adenine, 7-deaza-adenine, guanine, 7-deaza-guanine, uracil, cytosine, hypoxanthine and 7-deaza-hypoxanthine.

18. A compound according to claim 10 of the formula

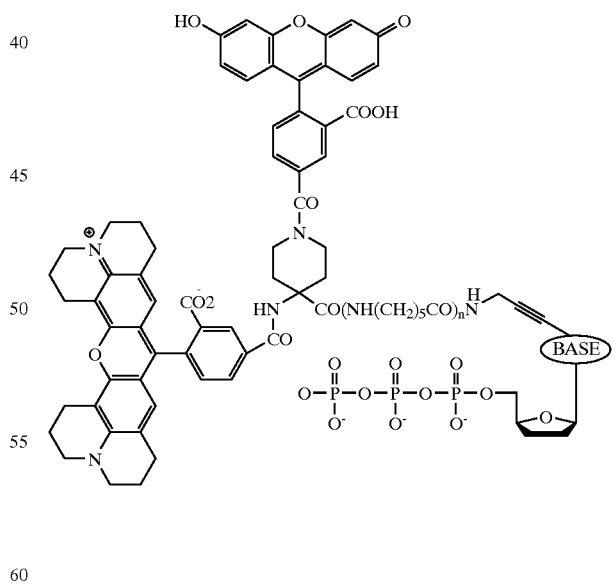

wherein

BASE is selected from the group consisting of adenine, 7-deaza-adenine, guanine, 7-deaza-guanine, uracil, cytosine, hypoxanthine and 7-deaza-hypoxanthine.

19. A compound according to claim 10 of the formula

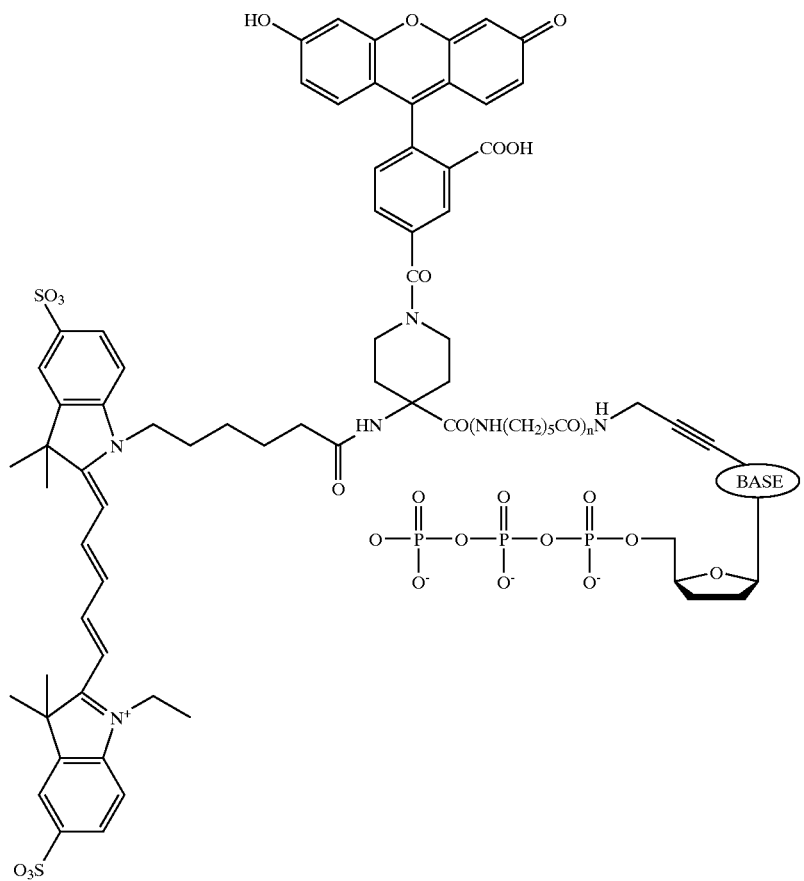
wherein
BASE is selected from the group consisting of adenine, 7-deaza-adenine, guanine, 7-deaza-guanine, uracil, cytosine, hypoxanthine and 7-deaza-hypoxanthine.
* * * * *